(12) United States Patent
Zhang et al.

(10) Patent No.: US 10,768,100 B2
(45) Date of Patent: Sep. 8, 2020

(54) AIR POLLUTION MONITORING SYSTEM AND AIR POLLUTION MONITORING METHOD

(71) Applicants: Weimin Zhang, Suzhou (CN); Mengying Zhang, Suzhou (CN)

(72) Inventors: Weimin Zhang, Suzhou (CN); Mengying Zhang, Suzhou (CN)

( * ) Notice: Subject to any disclaimer, the term of this patent is extended or adjusted under 35 U.S.C. 154(b) by 162 days.

(21) Appl. No.: 16/004,303

(22) Filed: Jun. 8, 2018

(65) Prior Publication Data

US 2019/0113445 A1 Apr. 18, 2019

(30) Foreign Application Priority Data

Oct. 16, 2017 (CN) .......................... 2017 1 0959360

(51) Int. Cl.
  *G01N 21/3504* (2014.01)
  *G08B 21/12* (2006.01)
  (Continued)

(52) U.S. Cl.
  CPC ....... *G01N 21/3504* (2013.01); *G01N 1/2273* (2013.01); *G01N 33/0031* (2013.01);
  (Continued)

(58) Field of Classification Search
  CPC .. G01W 1/02; G01W 2001/006; G08B 21/12; G08B 21/182; G01N 2021/3513;
  (Continued)

(56) References Cited

U.S. PATENT DOCUMENTS

| 4,204,121 A | * | 5/1980 | Milly | ................... | G01N 1/2273 |
| | | | | | 250/338.5 |
| 4,555,627 A | * | 11/1985 | McRae, Jr. | ............. | G01M 3/38 |
| | | | | | 250/330 |

(Continued)

OTHER PUBLICATIONS

Shaban et al., "Urban Air Pollution Monitoring System With Forecasting Models", Apr. 2016, IEEE Sensors Journal, vol. 16, No. 8, pp. 2598-2606. (Year: 2016).*

(Continued)

*Primary Examiner* — David P Porta
*Assistant Examiner* — Jeremy S Valentiner
(74) *Attorney, Agent, or Firm* — SZDC Law P.C.

(57) ABSTRACT

A plurality of monitoring devices are arranged at different heights and steps, and infrared reflective assemblies of the monitoring device are set at different heights to collect infrared spectral data of chemical constituents of the air mass that are being diffused in airspace of different heights. The pollution factors contained in the air mass and the pollution level of each factor are learned by using IR spectrum for qualitative and quantitative analysis on the pollution factor, therefore realizing continuous monitoring in a certain area. Artificial duty is not required while 24-hour continuous intelligent monitoring can be achieved. Besides, meteorological data are collected in combination with the meteorological data collected by the meteorological information acquisition module at different heights and calculation is made based on the air diffusion model of various pollution factors to finally determine the position of air pollution source.

9 Claims, 6 Drawing Sheets (51) Int. Cl.
- *G01N 1/22* (2006.01)
- *G01N 33/00* (2006.01)
- *G01W 1/00* (2006.01)
- *G08B 21/18* (2006.01)
- *G01W 1/02* (2006.01)
- *G01N 21/35* (2014.01)

(52) U.S. Cl.
CPC ............. *G01W 1/02* (2013.01); *G08B 21/12* (2013.01); *G08B 21/182* (2013.01); *G01N 2021/3513* (2013.01); *G01N 2021/3595* (2013.01); *G01W 2001/006* (2013.01); *Y02A 50/24* (2018.01)

(58) Field of Classification Search
CPC ......... G01N 2021/3595; G01N 1/2273; G01N 33/0031; Y02A 50/24
See application file for complete search history.

(56) References Cited

U.S. PATENT DOCUMENTS

| | | | |
|---|---|---|---|
| 5,210,702 A * | 5/1993 | Bishop | G01N 21/33 250/338.5 |
| 2011/0122397 A1* | 5/2011 | Wong | G01S 15/885 356/51 |
| 2018/0321208 A1* | 11/2018 | Bai | G06N 20/00 |

OTHER PUBLICATIONS

Hall, "Case Study:Environmental Monitoring Using Remote Optical Sensing (OP-FTIR) Technology at the Oklahoma City Air Logistics Center Industrial Wastewater Treatment Facility", Apr. 2004, Federal Facilities Environmental Journal, vol. 15, Iss. 1, pp. 21-37 (Year: 2004).*

* cited by examiner

AIR POLLUTION MONITORING SYSTEM AND AIR POLLUTION MONITORING METHOD

This application claims priority to Chinese Patent Application No.: 201710959360.8, filed on Oct. 16, 2017, which is incorporated by reference for all purposes as if fully set forth herein.

TECHNICAL FIELD

The invention relates to a monitoring system and monitoring method for air pollution, which is part of the air quality monitoring area.

BACKGROUND TECHNOLOGY

At present, the world is faced with the most serious environmental problem of air pollution, which is particularly serious in China. Among the many sources of air pollution, the chemical park pollution has to be settled urgently at this stage. Exhaust gas from the chemical park contains various chemical factors, and its emission directly affects the life health of surrounding residential areas.

At this stage, traditional monitoring equipment applied for exhaust emission from chemical industry parks mainly operates in the form of point-based monitoring and passive monitoring. Since the monitoring factor is relatively single and the equipment is fixed on the ground, the exhaust diffusion from chemical industry parks causes traditional monitoring equipment to fail to conduct comprehensive monitoring. The existing air monitoring equipment and monitoring stations are mainly on the ground. The monitoring altitude is generally lower than 5 m, and the diffusion trajectory of pollution factors is generally higher than 10 m in low and medium altitude airspace. Therefore, the existing monitoring tools can neither reflect the real situation of exhaust emission in the park, nor implement management, prevention or control of the emission; it is impossible to detect and solve problems of underlying discharge, overflow discharge and emergent environmental problems in time against supervision.

In addition, due to the significant influence of meteorological conditions and production processes, the air pollutant emission has characteristics of paroxysmal and transient. Therefore, technicians in the area are devoted to the development of a technology for real-time online continuous monitoring of the initial state of air pollution. Such real-time online continuous monitoring of characteristic pollutant concentrations will certainly become an effective tool for the supervision of air pollutants by local government departments, environmental protection monitoring departments, and related production process companies.

SUMMARY OF THE INVENTION

The object of the invention is to provide a stereoscopic FTIR vertical radial monitoring system capable of realizing intelligent monitoring of air pollution.

To achieve the above object, the present invention provides the following technical solution: a monitoring system for air pollution, which is used to monitor the air quality in a certain area, including:

Multiple monitoring equipment, pollution factor qualitative modules and pollution factor quantification modules;

Each of the monitoring equipment includes at least one infrared reflective assembly set at different heights and infrared emission hosts simultaneously corresponding to at least one such assembly. The infrared emission host emits infrared rays to the corresponding infrared reflective assembly, and each monitoring equipment monitors the air mass in its monitoring range in real time to obtain the infrared spectral data of the passing gas clusters.

The pollution factor qualitative module presets the infrared judgment reference data of a plurality of pollution factors, which uses the infrared spectrum values of a plurality of different pollution factors as a reference. The pollution factor qualitative module compares the above reference data with the infrared spectral data obtained by the monitoring equipment to analyze and obtain the pollution factors contained in the scope monitored by the corresponding monitoring equipment.

The pollution factor quantification module is preset with pollution amount determination reference data corresponding to a plurality of different pollution factors, which is classified into different pollution amount levels according to the amount of the pollution factor in the air mass. The quantitative module determines the reference data based on the infrared spectral data of the chemical factors obtained by the monitoring equipment, the pollution factor analyzed by the quantification module, and the pollution quantity preset in the quantitative module, and analyzes to achieve the pollution level within the scope monitored by the corresponding monitoring equipment.

Furthermore, the air pollution monitoring system also includes:

The weather information collection module collects the weather data in a certain area, including wind direction, wind speed, temperature, air pressure and humidity;

Furthermore, the air pollution monitoring system also includes:

The traceability judgment module is respectively connected to a plurality of monitoring equipment and weather information collection module signals to obtain the pollution factors and pollution levels in the monitored area of each monitoring equipment on the basis of the wind direction and speed, temperature, pressure and humidity collected by the weather information collection module within the corresponding period. The traceability judgment module performs calculation based on the natural diffusion law of various pollution factors to determine the location of the pollution source.

Furthermore, each of the monitoring equipment corresponds to a weather information collection module, which is placed aside the infrared emission host of the corresponding monitoring equipment.

Furthermore, the air pollution monitoring system as mentioned in Clause 1 is characterized in that it comprises an early warning equivalent module that is connected to signals of the pollution factor quantification module. The early warning equivalent module presets a warning threshold corresponding to different pollution levels according to the distance between the infrared emission host and the infrared reflective component. The pollution factor quantification module will compare the pollution level of each pollution factor detected by the corresponding monitoring equipment with the warning threshold in the early warning equivalent module. If the air pollution level exceeds the warning threshold, the warning equivalent module will issue an early warning signal.

Furthermore, the infrared reflective assembly is placed at vertical height of 3 to 50 meters.

Furthermore, according to the height of the monitoring equipment, its scanning mode works as follows: scan within a scope of vertical angles of −65°~+65° at height of 3~50 meters, or within a scope of horizontal angles of 360° at a height of 10~50 meters.

Furthermore, according to the height of the monitoring equipment, its scanning mode works as follows: scan within a scope of vertical angles of 1°~45° at height of 3~50 meters, or within a scope of horizontal angles of −65°~45° at a height of 10~50 meters.

Furthermore, the air pollution monitoring system comprises a fixed tower of infrared reflective assemblies. A plurality of infrared reflective assemblies is fixed at different heights so that the infrared rays emitted by the infrared emission host can be scanned up and down in the height direction of the fixed tower.

Furthermore, a plurality of infrared reflective assemblies is arranged in a stepwise manner to form different heights of monitoring.

Furthermore, the amount of the meteorological information acquisition module is multiple and a plurality of meteorological information acquisition modules are arranged in a stepwise manner to form different heights of monitoring.

The invention also provides an air pollution monitoring method. It employs a plurality of monitoring equipment, each of which includes a plurality of infrared reflective assemblies set at different heights and infrared emission hosts simultaneously corresponding to such assemblies. The monitoring method includes the following steps:

Each infrared emission host emits infrared rays to a corresponding plurality of the infrared reflective assemblies to monitor the air mass in the monitored range of the monitoring equipment in real time to obtain the infrared spectral data of the chemical factors in the passing air mass.

According to such infrared spectral data monitored by each monitoring equipment within a set time, analyze the pollution factors contained in the air masses, calculate the amount of pollution factors in the air masses, and then determine the pollution level within the scope monitored by the monitoring equipment.

Furthermore, the monitoring method includes the following steps:

Acquire weather data within the monitored scope of each monitoring equipment, including wind direction, wind speed, temperature, air pressure, and humidity;

Furthermore, the monitoring method includes the following steps: according to the law of natural diffusion of various pollution factors, determine the position of the pollution source based on the wind direction, wind speed, temperature, pressure and humidity in the corresponding time.

Furthermore, the monitoring method comprises the following steps: compare each pollution level with a warning threshold and send a warning signal when the pollution level exceeds the warning threshold.

The present invention has the active effects as follows: the monitoring system and monitoring method for air pollution of the invention are provided with a plurality of monitoring devices and the infrared reflecting components of the monitoring devices set at different heights to collect infrared spectral data of chemical constituents of the air mass that are being diffused in airspace of different heights. Then the pollution factors contained in the air mass and the pollution level of each factor are learned by using IR spectrum for analysis and qualitative and quantitative analysis on the pollution factor, therefore realizing continuous monitoring in a certain area. Artificial duty is not required while 24-hour continuous intelligent monitoring can be achieved. The above-mentioned monitoring system and monitoring method for air pollution also collect weather information, and then determine the location of the pollution source based on calculations of the diffusion laws of various pollution factors.

The technical solutions of the present invention are summarized in the above part. In order to more clearly understand the technical means of the invention and implement as required by the specifications, the following part lists examples of the invention as well as drawings of detailed description.

SPECIFIC IMPLEMENTATION MODE

The specific implementation of the present invention will be further described in detail below with reference to the drawings and examples. The following examples are intended to illustrate the present invention but are not intended to limit the scope of the invention.

Figure 1:
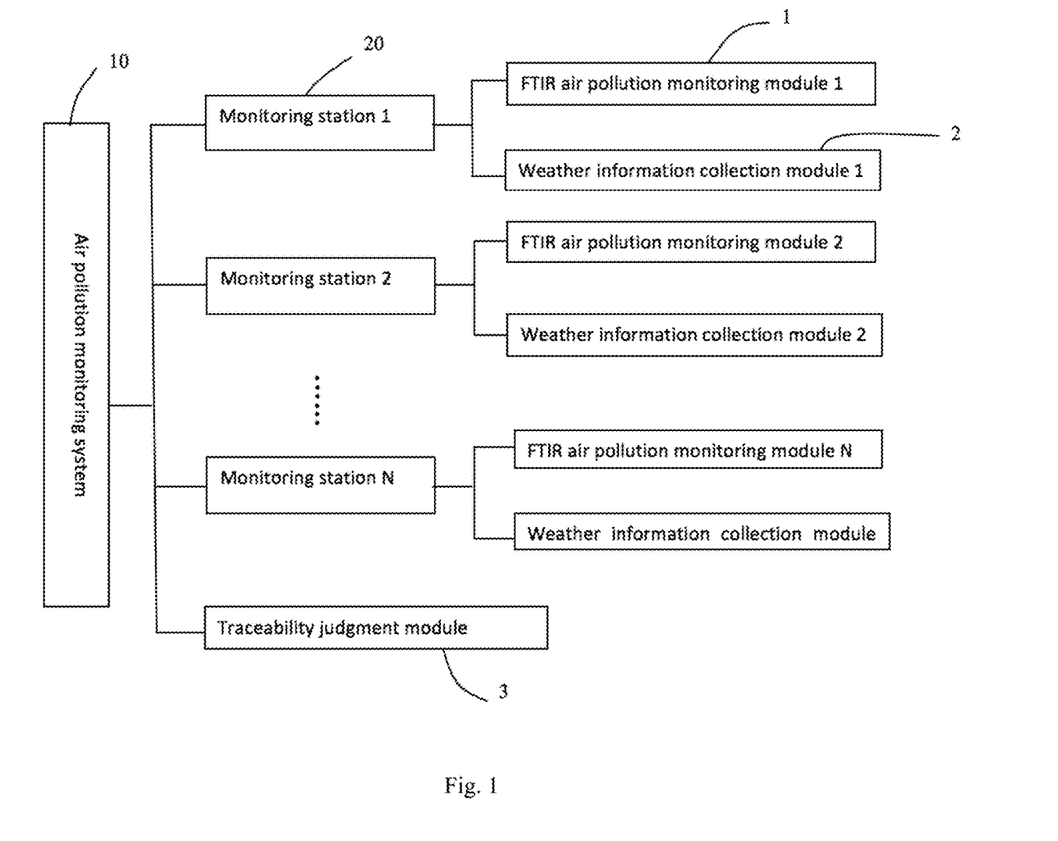
FIG. 1 shows a structure chart of an example of using the invention of an air pollution monitoring system.
Figure 5:
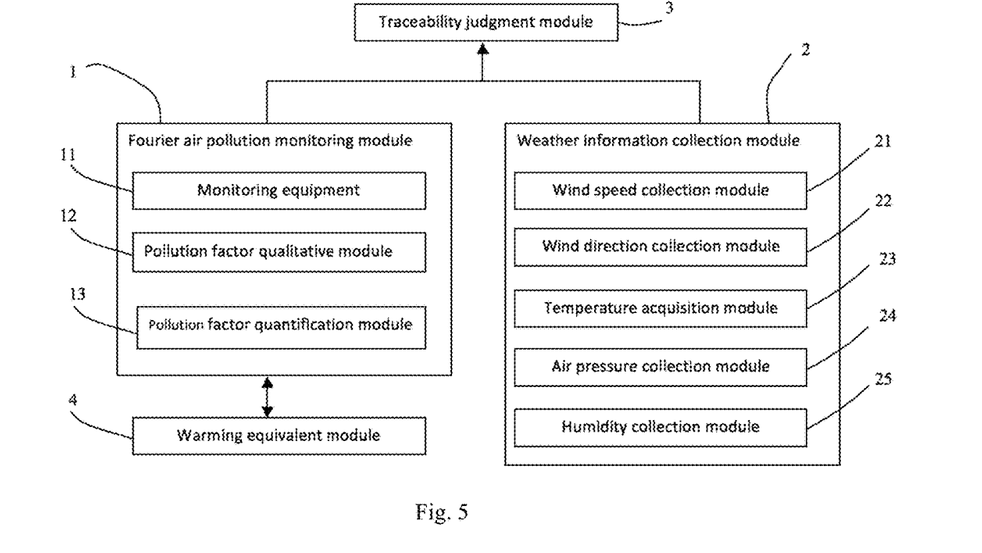
FIG. 5 is a partial module diagram of the air pollution monitoring system shown in FIG. 1.

Referring to FIG. 1 and FIG. 5, the air pollution monitoring system 10 as shown in a preferred example of implementing the present invention is used to monitor the air quality in a certain area (which may be a chemical industry park). The air pollution monitoring system 10 includes several monitoring stations 20 and the source determination module 3 connected to signals of these monitoring stations 20. Each monitoring station 20 includes a Fourier air pollution monitoring module 1 (FTIR) and a weather information collection Module 2.

Figure 4:
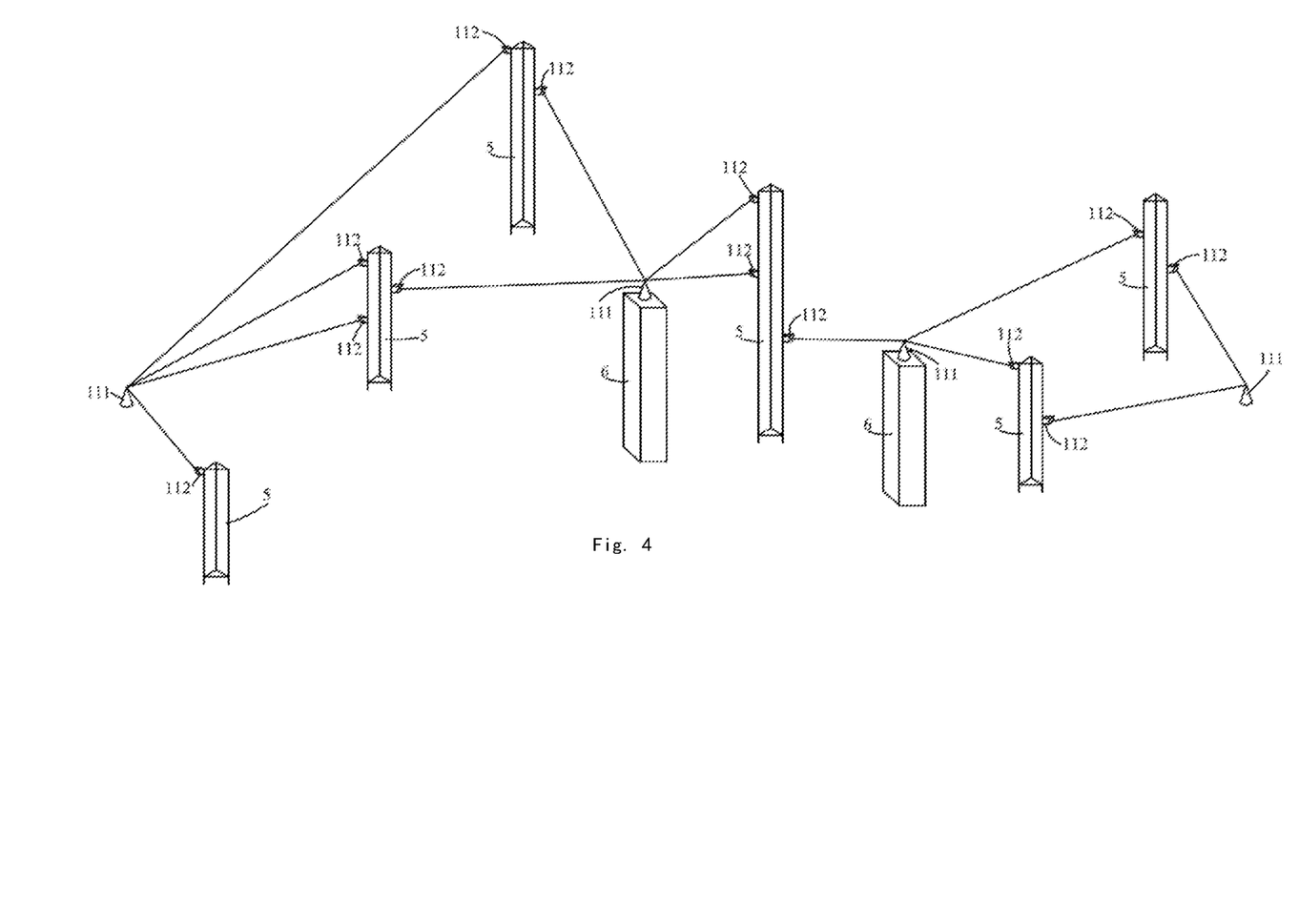
FIG. 4 is another practical diagram for implementing the air pollution monitoring system shown in FIG. 1.

In this example, each Fourier air pollution monitoring module 1 includes a monitoring equipment 11, a pollution factor qualitative module 12, and a pollution factor quantitative module 13. Each of the monitoring equipment 11 includes a plurality of infrared reflector assemblies 112 and an infrared emission host 111 set at the same time corresponding to these assemblies 112, each of which is set at different heights. Each infrared emission host 111 emits infrared rays to a corresponding infrared reflective assembly 112 to monitor the air mass in the monitored range of the monitoring equipment 11 in real time to obtain the infrared spectral data of the chemical factors in the passing air mass. The pollution factor qualitative module 12 presets the infrared judgment reference data of a plurality of pollution factors, which uses the infrared spectrum values of a plurality of different pollution factors as a reference. The pollution factor qualitative module compares the above reference data with the infrared spectral data obtained by the monitoring equipment 11 to analyze and obtain the pollution factors contained in the scope monitored by the corresponding monitoring equipment 11. The pollution factor quantification module 13 is preset with pollution amount determination reference data corresponding to those preset in the pollution factor qualitative module 12 of a plurality of different pollution factors, which is classified into different pollution amount levels according to the amount of the pollution factor in the air mass. Such quantification module 13 determines the reference data based on the infrared spectral data of the chemical factors obtained by the monitoring equipment 11, the pollution factor analyzed by the qualitative module 12, and the pollution quantity preset in the quantification module 13, and analyzes to achieve the pollution level within the scope monitored by the corresponding monitoring equipment 11. In this example, the vertical height of the monitoring equipment 11 ranges from 3 to 50 meters. According to the height of the monitoring equipment, its scanning mode works as follows: scan within a scope of vertical angles of −65°~85° at height of 3~50 meters, or within a scope of horizontal angles of 360° at a height of 10~50 meters. In a particular embodiment, the common scanning mode works as follows: scan within a scope of vertical angles of 1°~45° at height of 3~50 meters, or within a scope of horizontal angles of −65°~45° at a height of 10~50 meters. The infrared reflective assembly 112 of the monitoring equipment 11 is fixed by the fixed tower 5, and the infrared emission host 111 of the detection device 11 is set on the station building 6, which may be a general building construction, or may be specifically used for fixing infrared emission. Certainly, in other examples, the host 111 can also be fixed on the fixed tower 5. In other examples, in order to adjust the position of the infrared emission host 111 and/or the infrared reflective assembly 112 of the monitoring equipment 11, such host 111 and/or the assembly 112 may moves along the height direction of the fixed tower 5. The monitoring height can be adjusted according to the position of 111 and 112, thus the air pollution monitoring system 10 can be more flexible. The fixed tower 5 is a prismatic structure. In this example, the fixed tower 5 is a triangular prism, which has three planes perpendicular to the ground. The shape of triangular prism helps the fixed tower 5 to set a plurality of infrared reflective assemblies 112 on multiple angles of the fixed tower 5, and multiple such assemblies 112 won't interfere with each other. Infrared rays emitted from the infrared emission host 111 to the infrared reflective assemblies 112 will not be sheltered. The infrared emission host 111 and the infrared reflective assemblies 112 will not be sheltered by any part of the fixed tower 5. Please refer to FIG. 4 and FIG. 5 In this example, most of the infrared reflective assemblies 112 of the monitoring equipment 11 are fixed and arranged at different heights by the fixed tower 4. The infrared rays from the infrared emission host 111 can be emitted up and down at the height of the fixed tower 4. A plurality of infrared reflective assemblies 112 are arranged in a stepwise manner.

Figure 2:
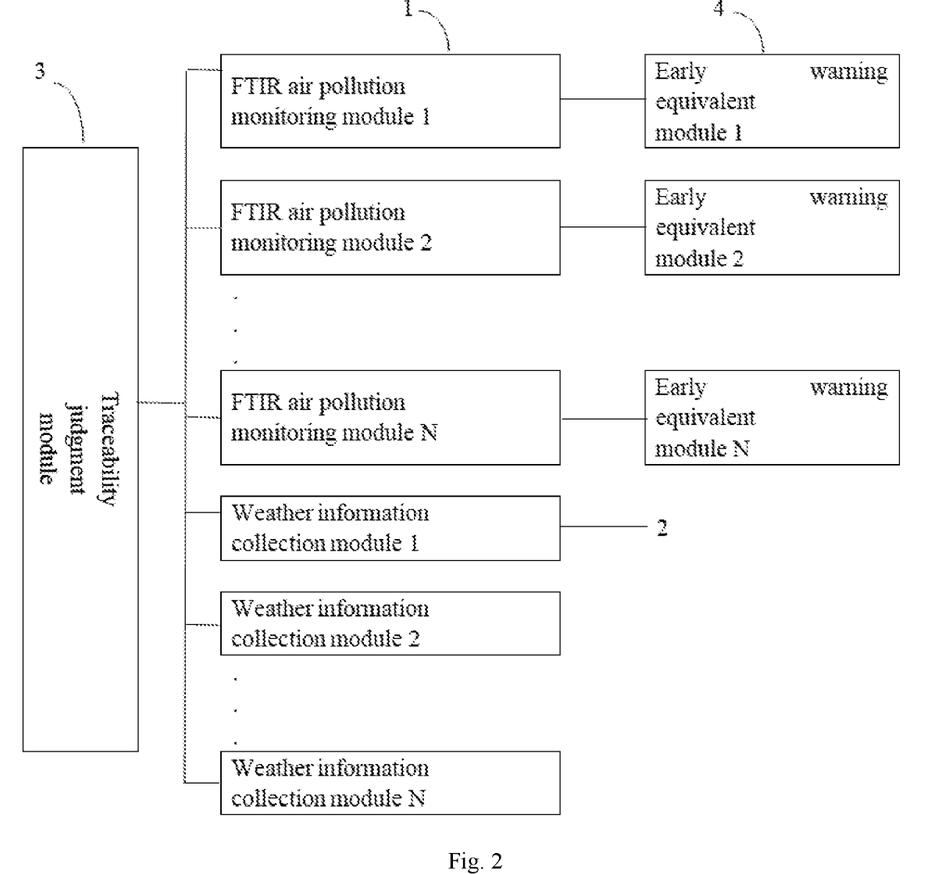
FIG. 2 shows a module diagram of an example of using the invention of an air pollution monitoring system.
Figure 3:
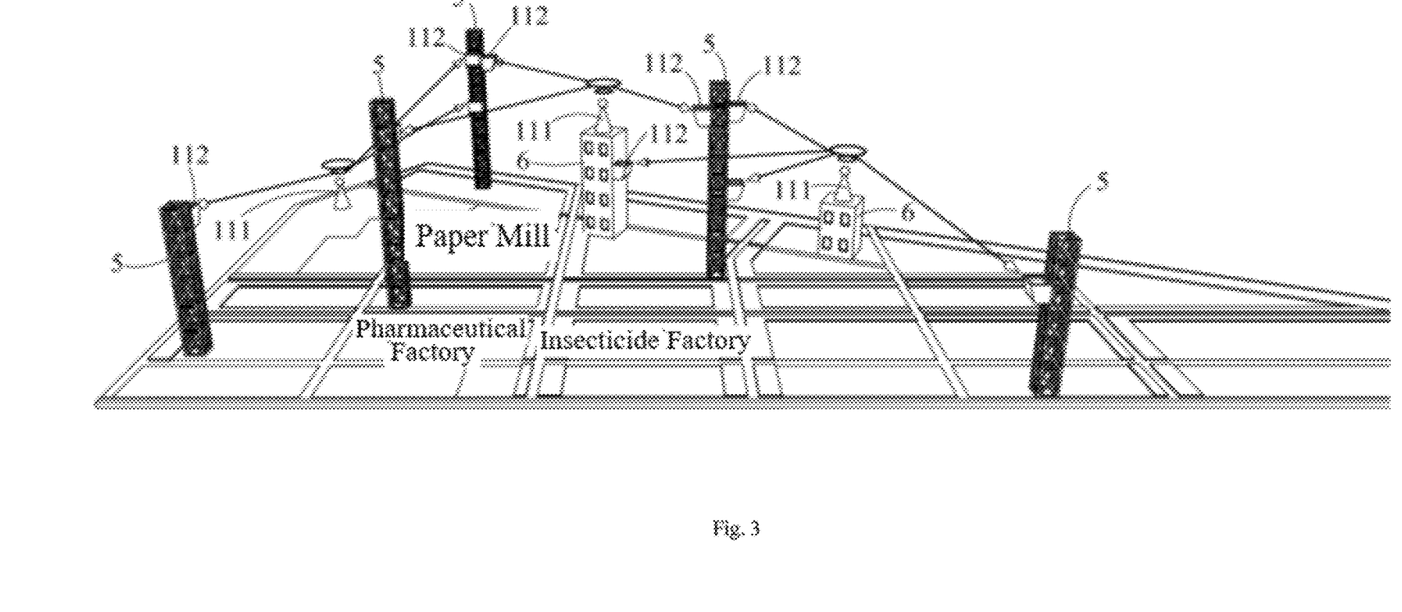
FIG. 3 shows a practical diagram of an example of using the invention of an air pollution monitoring system.

The weather information collection module 2 is used to collect five weather parameters in the monitoring area, including wind direction, wind speed, temperature, air pressure and humidity. There is a plurality of meteorological information acquisition modules in which to correspond to a plurality of the monitoring equipment, and each of the monitoring equipment is connected to a weather information collection module 2. The weather information collection module 2 may comprises a wind direction acquisition module 21 for acquiring the wind direction, a wind speed acquisition module 22 for acquiring the wind speed, a temperature acquisition module 23 for acquiring the temperature, an air pressure acquisition module 24 for acquiring the air pressure, and a humidity acquisition module 25 for acquiring the humidity. Explanation of meteorological factors: according to the five weather parameters acquired at different heights and their difference with the weather parameters acquired on the ground, we can monitor the emission trend and diffusion condition for the chemical factors, and locate the pollution source accurately.

1. Wind speed: As the height increases, the wind force becomes higher and the diffusion of chemical factors becomes faster.

| Wind scale corresponding to different heights | | |
| --- | --- | --- |
| Ground | 10-30 m | 30-50 m |
| Grade 1 | Grade 2 | Grade 3 |
| Grade 2 | Grade 3 | Grade 4 |
| Grade 3 | Grade 4 | Grade 5 |
| Grade 4 | Grade 5 | Grade 6 |
| Grade 5 | Grade 7 | Grade 8 |
| Grade 6 | Grade 8 | Grade 9 |
| Grade 7 | Grade 9 | Grade 10 |
| Grade 8 | Grade 10 | Grade 12 |
| Grade 9 | Grade 11 | Grade 13 |
| Grade 10 | Grade 13 | Grade 14 |

The wind on the ground is generally below grade 5, and in general, the higher the height, the greater the wind speed, so the wind speed at 10-30 meters is obviously higher than the surface wind speed. As the height increases, the wind force becomes higher. Therefore, it is not only necessary to refer to the local ground wind speed, but also to consider the wind speed at high altitude to ensure that the wind speed is within the range. Therefore, the weather information collection modules are installed at different heights so as to monitor the diffusion condition of the chemical factors on the monitoring optical path of the same height more accurately.

2. Wind direction:

Wind directions at different heights reflecting the diffusion direction of both organized and disorganized exhaust gases helps to locate the source of the exhaust gases.

In the ground layer with a height of 10-50 meters, the wind direction will change obviously in the short time due to the obstruction of buildings and the decrease of ground friction. In the industrial park, because the enterprise production generates the local heat island effect in a range, all kinds of organized and unorganized exhaust emissions will slow down and interfere with the local wind direction.

3. Humidity

The vertical distribution of relative humidity is closely related to whether there is cloud in the air, and it also depends on whether the air has ascending motion. In the clear sky, if the atmosphere does not rise obviously, the relative humidity in the air will decrease progressively. In cloudy conditions, the relative humidity in the clouds is the larger but with the increase of cloud height, the relative humidity decreases. On rainy days, the lower the clouds, the greater the humidity, and the slower the diffusion of chemical factors.

The air humidity in the industrial park is different from the air humidity outside the park. It is not only affected by meteorological conditions, but also affected by the enterprises. In the chemical industrial park, the water vapor discharged by enterprise production affects the distribution and diffusion of water vapor in the chemical industrial park, which leads to the different water vapor content in different regions and the different air humidity. Consequently, humidity values at different heights may vary with the influence of the water vapor discharged by the enterprises in or near the industrial park. Since the higher the humidity, the slower the exhaust gas diffuses in the air, it is very necessary to collect the data of air humidity on the optical path of different heights to well understand the extent of the influence to which chemical factors diffuse in this pathway.

4. Temperature

In general, the higher the altitude, the lower the temperature, the lower the humidity.

For air saturated with water vapor, the temperature drops 0.6 degrees for 100 meters (adiabatic rate).

Relationship between height and temperature: about 0.6 C/100 m $$T=T_0 \cdot (6*H)$$

T: temperature aloft; To: surface temperature; H: height, unit: km

Without considering other factors, the height is increased by 50 meters and the temperature difference is 0.3° C.

The higher the temperature is, the higher the saturated vapor pressure of the air is, that is, the air at high temperature can hold more vaporous water than the low temperature air.

Accordingly, the vertical distribution of atmospheric temperature near the ground determines the atmospheric stability, which further influences the atmospheric turbulence, so as to make an effect to the diffusion of the air pollution. Hence, the vertical distribution of atmospheric temperature is closely related to the degree of the air pollution.

5. Air Pressure

Although the air pressure of the industrial park is affected by the factors such as the installation height of the weather information collection module, temperature, humidity and so on, it still has a strong influence on the diffusion of the air pollutants. Higher temperature and lower air pressure near the ground make the air flow rise up to undermine the stability of the vertical air distribution so as to accelerate the diffusion and dilution of the air pollutants. Conversely, if the temperature inversion occurs, and the air pressure near the ground is increased, during which time the weather becomes clear, and the wind speed is declined, the diffusion of the pollutants will be impeded.

As the meteorological data of different heights will change, in order to improve the monitoring accuracy, a plurality of the meteorological information acquisition modules 2 are arranged in a stepwise manner to form different monitoring heights in the present embodiment.

The infrared emission host 111 and the weather information collection module 2 are integrated to realize three-dimensional configuration of the multi-faceted and multi-point meteorological devices in the monitoring area together with the monitoring equipment 11 at different heights (5~50 m). The three-dimensional monitoring regional meteorological monitoring system can analyze the impact of meteorological conditions on pollution diffusion in real time and improve the scientificity, rationality and reliability of the monitoring data. Comparing with other monitoring technologies at home and abroad, this air pollution monitoring system 10 for air pollution has greater advantages for the complete reflection of regional air pollution.

Figure 6:
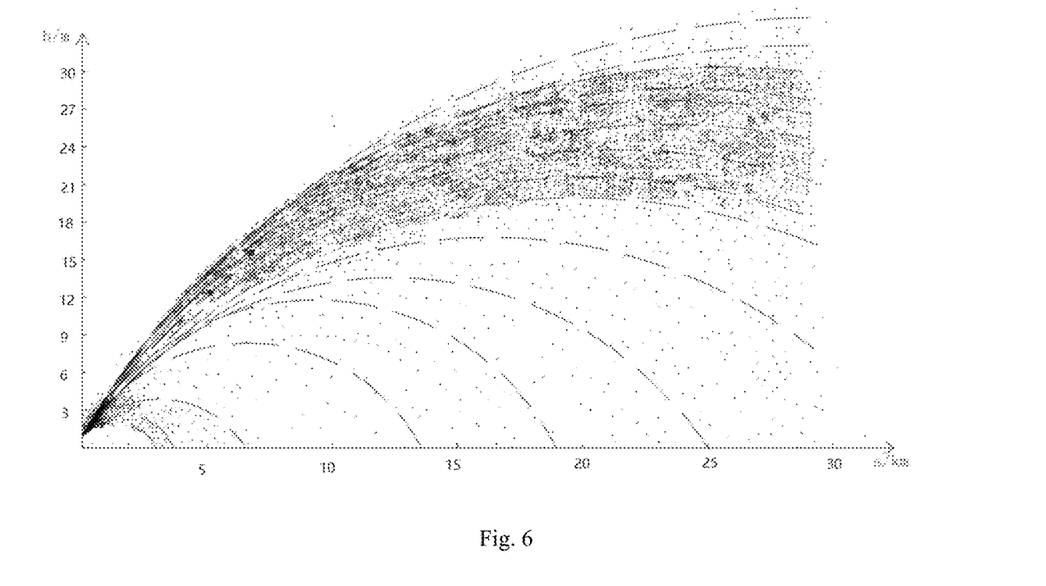
FIG. 6 is a schematic diagram of the diffusion law of various pollution factors, wherein h in the longitudinal direction represents the height of the emission of pollutants, and m in the lateral direction represents the distance of the original point of the emission source at the location of the pollution factor.

The traceability judgment module 3 is respectively connected to a plurality of monitoring equipment 11 and weather information collection module 2 signals to obtain the pollution factors and pollution levels in the monitored area of each monitoring equipment 11 on the basis of the wind direction and speed, temperature, pressure and humidity collected by the weather information collection module 2 within the corresponding period. The traceability judgment module 3 performs calculation based on the natural diffusion law of various pollution factors to determine the location of the pollution source. The air diffusion model is established through a large number of monitoring and analysis of the natural diffusion law of various pollution factors and data processing. Please refer to FIG. 6. The diffusion of various pollution factors is affected by the wind direction, wind speed, temperature, pressure, humidity and the proportion of pollution factors. The diffusion law of various pollution factors can be known through preliminary experiments.

In this example, the air pollution monitoring system 10 for air pollution further includes an early warning equivalent module 4 connected to signals of the pollution factor quantifying module 13. The early warning equivalent module 4 presets a warning threshold corresponding to different pollution levels according to the distance between the infrared emission host and the infrared reflective component. The pollution factor quantification module 13 will compare the pollution level of each pollution factor detected by the corresponding monitoring equipment 11 with the warning threshold in the early warning equivalent module 4. If the air pollution level exceeds the warning threshold, the warning equivalent module 4 will issue an early warning signal. The early warning signals issued by the early warning equivalent module 4 can serve as an early warning to check the pollution in time.

Figure 7:
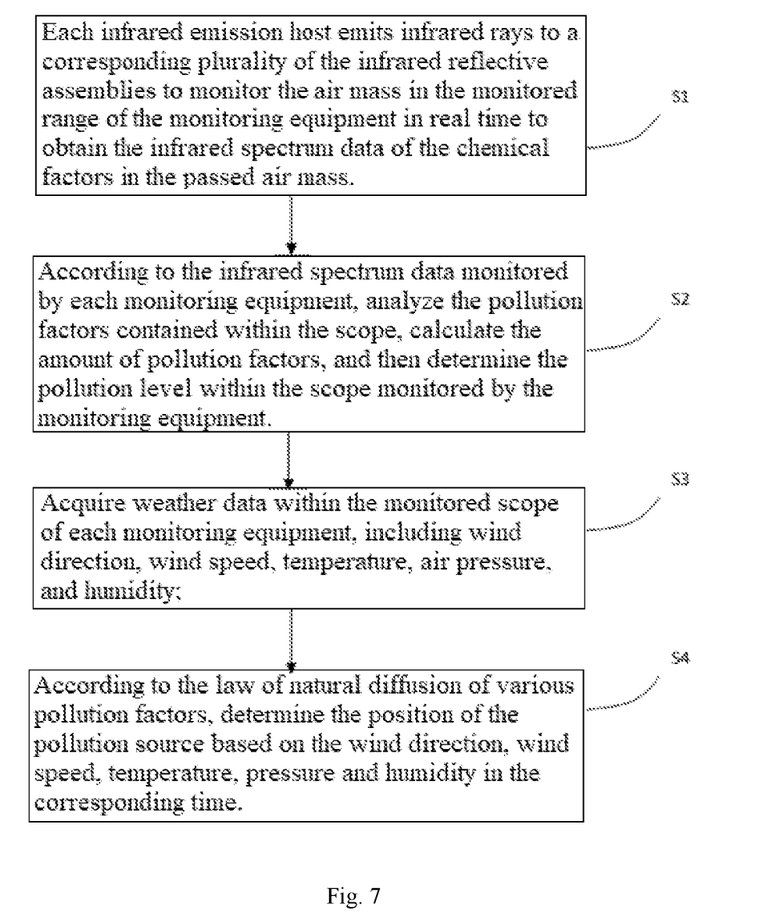
FIG. 7 is a flowchart of an example of using the invention of an air pollution monitoring method.

Referring to FIG. 7 in combination with FIG. 1 to FIG. 5, an air pollution monitoring method shown in the example of the present invention is used to monitor the air in a certain area. The monitoring method may use the above air pollution monitoring system 10. It uses a plurality of monitoring modules including monitoring equipment 11, each of which includes a plurality of infrared reflective assemblies 112 and an infrared emission host 111 placed correspondingly to such assemblies 112 at the same time. These assemblies 112 are set at different heights. The monitoring method includes the following steps:

S1: Each infrared emission host 111 emits infrared rays to a corresponding plurality of the infrared reflective assemblies 112 to monitor the air mass in the monitored range of the monitoring equipment 11 in real time to obtain the infrared spectral data of the chemical factors in the passing air mass.

S2: According to such infrared spectral data monitored by each monitoring equipment 11 within a set time, analyze the pollution factors contained in the air masses, calculate the amount of pollution factors in the air masses, and then determine the pollution level within the scope monitored by the monitoring equipment 11.

S3: Acquire weather data within the monitored scope of each monitoring equipment 11, including wind direction, wind speed, temperature, air pressure, and humidity;

S4: Calculate and determine the position of the pollution source according to the law of natural diffusion of various pollution factors, as well as the wind direction, wind speed, temperature, pressure, and humidity in the corresponding time. Diffusion of various pollution factors is affected by wind direction, wind speed, temperature, pressure and humidity, and the proportion of polluting factors. The diffusion rules of various pollution factors can be known through preliminary experiments. See FIG. 6, for example, the initial effective diffusion height of the dense diffusion zone of benzene series, hydrogen and VOC compound is 10 to 50 meters, 1-5 kilometers away from the pollution source in the air. In this step, the natural diffusion law of various pollution factors can be modeled. Then, the air diffusion model is used to determine the location of the pollution source based on the wind direction, wind speed, temperature, atmospheric pressure, and humidity during the corresponding time. The air diffusion model is established in advance through extensive monitoring and analysis of the natural diffusion laws of various pollution factors and data processing.

During the specific implementation process, the order of the above steps S2 and S3 may be exchanged, or S1 and S3 may be performed simultaneously. The above-mentioned monitoring method for air pollution can be realized by the air pollution monitoring system 10, and the structure of the air pollution monitoring system 10 will be further described herein.

In this example, the monitoring method further comprises the following steps: compare each pollution level with a warning threshold and send a warning signal when the pollution level exceeds the warning threshold. The early warning signals issued by this way can serve as an early warning to check the pollution in time.

In summary, the above-mentioned air pollution monitoring system 10 and monitoring method for air pollution are provided with a plurality of monitoring devices 11 and the infrared reflecting components 112 of the monitoring devices 11 set at different heights to collect infrared spectral data of chemical constituents of the air mass that are being diffused in airspace of different heights. Then the pollution factors contained in the air mass and the pollution level of each factor are learned by using IR spectrum for analysis and qualitative and quantitative analysis on the pollution factor, therefore realizing continuous monitoring in a certain area. Artificial duty is not required while 24-hour continuous intelligent monitoring can be achieved. The above-mentioned air pollution monitoring system 10 and monitoring method for air pollution also collect weather information, and then determine the location of the pollution source based on calculations of the diffusion laws of various pollution factors.

The above example breaks through the traditional practice of ground monitoring along the boundary of an industrial park (plant), 10-50 meters A It sets three-dimensional infrared monitoring network combining a certain number of infrared emission hosts 111 and a corresponding infrared reflective assembly 112 with a weather information acquisition module 2 in a certain height of 10~50 meters in a stepwise order within the park (plant) according to the law of natural diffusion of various pollution factors in their initial stages. It then performs qualitative and quantitative analysis on the pollution factors in the initial diffusion state in chemical plants in the park (plant). The infrared monitoring data and meteorological data obtained will be used as the basis for the source determination module 3 to truly achieve the purpose of early warning.

The technical features of the above examples can be arbitrarily combined within an industrial park (plant). Not all possible combination of the technical features in the above examples are described for the purpose of conciseness. However, provided that no contradiction is found in the combination of features, such combination should be considered as within the scope described herein.

The above examples merely represent several ways to implement the present invention. The description is specific and detailed, but it cannot be construed as a limitation to the scope of the utility model patent. It should be noted that, for a person of ordinary skill in the art, several variations and improvements can be made without departing from the concept of the present invention, and these are all within the protection scope of the present invention. Therefore, the scope of protection of the utility model patent shall be subject to the appended claims.

The invention claimed is:

1. An air pollution monitoring system comprising:
a plurality of monitoring equipments, pollution factor qualitative modules, pollution factor quantitative modules, and a fixed tower;
wherein each of the monitoring equipments includes an infrared reflective assembly and an infrared emission host; at least one of the infrared reflective assemblies of each of the monitoring equipments is disposed at a different height; each of the infrared emission hosts emits infrared rays to the corresponding infrared reflective assemblies, and each monitoring equipment performs real time monitoring of an air mass within a monitoring scope to obtain an infrared spectral data of passing gas clusters;
the pollution factor qualitative modules are preset with an infrared judgment reference data of a plurality of pollution factors, which uses the infrared spectrum values of a plurality of different pollution factors as a reference; the pollution factor qualitative module compares the infrared judgment reference data with the infrared spectral data obtained by the monitoring equipment to analyze and obtain the pollution factors contained in the monitoring scope by the corresponding monitoring equipment;
the pollution factor quantification modules are preset with a pollution amount determination reference data corresponding to a plurality of different pollution factors, which is classified into different pollution amount levels according to the amount of the pollution factor in the air mass; the quantitative module determines a reference data based on the infrared spectral data obtained by the monitoring equipment, the pollution factor analyzed by the quantification module, and the pollution quantity preset in the quantitative module, and analyzes to achieve the pollution level within the monitoring scope by the corresponding monitoring equipment; and
the infrared reflective assemblies are fixed at different heights by the fixed tower so that the infrared rays emitted by the infrared emission host are scanned up and down in a vertical direction of the fixed tower.

2. The air pollution monitoring system of claim 1, further comprising:
a weather information collection module that collects a weather data in a certain area, including wind direction, wind speed, temperature, air pressure and humidity.

3. The air pollution monitoring system of claim 2, further comprising: a traceability judgment module that is respectively connected to the monitoring equipments and the weather information collection module,
wherein the traceability judgment module obtains the pollution factors and pollution levels in the monitored area of each monitoring equipment on the basis of the wind direction, wind speed, temperature, air pressure and humidity collected by the weather information collection module within a corresponding period; and the traceability judgment module performs a calculation based on the natural diffusion law of various pollution factors to determine the location of a pollution source.

4. The air pollution monitoring system of claim 2, wherein each of the monitoring equipments corresponds to one corresponding weather information collection module, which is placed aside the infrared emission host of the corresponding monitoring equipment.

5. The air pollution monitoring system of claim 1, further comprising:
- an early warning equivalent module that is connected to the pollution factor quantification module;
- wherein the early warning equivalent module is preset with a warning threshold corresponding to different pollution levels according to a distance between the infrared emission host and the infrared reflective component; and the pollution factor quantification module compares the pollution level of each pollution factor detected by the corresponding monitoring equipment with the warning threshold in the early warning equivalent module; if the pollution level exceeds the warning threshold, the warning equivalent module issues an early warning signal.

6. The air pollution monitoring system of claim 1, wherein the infrared reflective assembly is placed at a vertical height of 3 to 50 meters.

7. The air pollution monitoring system of claim 1, wherein a scanning mode of the monitoring equipments is: scan within a scope of vertical angles of −65° to +65° at height of 3 to 50 meters, or within a scope of horizontal angles of 360° at a height of 10 to 50 meters.

8. The air pollution monitoring system of claim 7 wherein the scanning mode is: scan within a scope of vertical angles of 1° to 45° at height of 3 to 50 meters, or within a scope of horizontal angles of −65° to 45° at a height of 10 to 50 meters.

9. The air pollution monitoring system of claim 1, wherein the infrared reflective assemblies are arranged in a stepwise manner.

\* \* \* \* \*